(12) United States Patent
Milella, Jr. et al.

(10) Patent No.: US 12,059,136 B2
(45) Date of Patent: Aug. 13, 2024

(54) CANNULATED ERGONOMIC DISPOSABLE PLASTIC BASE FOR MEDICAL INSTRUMENTS

(71) Applicant: ECA Medical Instruments, Inc., Newbury Park, CA (US)

(72) Inventors: Michael J Milella, Jr., Thousand Oaks, CA (US); Sarah Elizabeth Schaake, Centennial, CO (US)

(73) Assignee: ECA Medical Instruments, Inc., Newbury Park, CA (US)

( * ) Notice: Subject to any disclaimer, the term of this patent is extended or adjusted under 35 U.S.C. 154(b) by 1041 days.

(21) Appl. No.: 16/968,568

(22) PCT Filed: Feb. 9, 2019

(86) PCT No.: PCT/US2019/017387
§ 371 (c)(1),
(2) Date: Aug. 8, 2020

(87) PCT Pub. No.: WO2019/157402
PCT Pub. Date: Aug. 15, 2019

(65) Prior Publication Data
US 2021/0038205 A1    Feb. 11, 2021

Related U.S. Application Data

(60) Provisional application No. 62/628,886, filed on Feb. 9, 2018.

(51) Int. Cl.
*A61B 17/00* (2006.01)
*B25G 3/18* (2006.01)
*B25G 3/20* (2006.01)

(52) U.S. Cl.
CPC ............... *A61B 17/00* (2013.01); *B25G 3/18* (2013.01); *B25G 3/20* (2013.01); *A61B 2017/0023* (2013.01); *A61B 2017/00424* (2013.01)

(58) Field of Classification Search
CPC ........... A61B 17/00; A61B 2017/0023; A61B 2017/00424; A61B 17/8875; A61B 2017/00455; A61B 2017/0046; A61B 2217/007; B25G 3/18; B25G 3/20; B25G 1/007; B25G 1/102; B25B 23/0042
See application file for complete search history.

(56) References Cited

U.S. PATENT DOCUMENTS 986,761 A * 3/1911 Roscoe ................. B23B 31/103
                                                   403/301
4,752,292 A * 6/1988 Lopez ................ A61M 39/1011
                                                   604/905

(Continued)

*Primary Examiner* — Eugene T Wu
(74) *Attorney, Agent, or Firm* — Ferguson Case Orr Paterson LLP

(57) ABSTRACT

The disclosure includes a connection method to fluidly connect a fluid pathway in a handle is formed co-linearly or axially and connects to a lumen through a tool and shaft. The body and movable latch may be an integral single molded plastic part connected by a flexible. In operation actuating the movable latch to raise or lower a latching beak within a corresponding open guide in the plastic body. The shaft fits into a shaft guide in the body which intersects the beak guide to temporarily latch the shaft to the body via a mounting fixture the shaft with the beak; and, wherein the body has a face end and a tail end.

21 Claims, 16 Drawing Sheets

(56) References Cited

U.S. PATENT DOCUMENTS

| | | | |
|---|---|---|---|
| 5,797,897 A * | 8/1998 | Jepson | A61J 1/2089 604/533 |
| 5,810,792 A * | 9/1998 | Fangrow, Jr. | A61M 39/045 604/533 |
| 6,131,484 A | 10/2000 | Wang | |
| 9,855,059 B2 | 1/2018 | Dmuschewsky | |
| 2007/0205567 A1 | 9/2007 | Eberle | |
| 2012/0265177 A1 | 10/2012 | Beedall | |
| 2016/0354581 A1 | 12/2016 | Ivinson | |

* cited by examiner

CANNULATED ERGONOMIC DISPOSABLE PLASTIC BASE FOR MEDICAL INSTRUMENTS

CROSS-REFERENCE TO RELATED APPLICATION

This is a national phase application of International Patent Application No. PCT/US19/17387 filed on Feb. 9, 2019, which claims the benefit of U.S. Provisional Patent Application No. 62/628,886 filed Feb. 9, 2018. The entire contents of each of these applications are incorporated by reference herein.

BACKGROUND

1. Field

This disclosure relates to plastic disposable mounts to withstand forces applied to a shaft supporting a tool.

2. General Background

The medical industry has made use of both reusable and disposable tools and handles. In a surgical context, there is little room for error and the devices must be precise and simple for a surgeon to use during procedures.

Orthopedic surgical procedures can require the creation or enlargement of holes in bones, affixation or removal of fasteners and the like.

Reusable devices require constant recalibration and sterilization to avoid contamination.

DISCLOSURE

The present disclosure provides aspects of ergonomic quick release systems and methods including a plastic molded handle having a fluid pathway running axially therethrough with a front half section and a back half section; the front section comprising; a face end with an interface; a shaft guide collinear with the interface configured to accept a shaft; a beak guide with an open top and an open bottom generally perpendicular to the shaft guide and intersecting the shaft guide; a lumenated shaft with a distal end having a mounting fixture and a proximal end configured to mate with the shaft guide; a plastic flexible region hinge portion integrally formed as part of the front half; a plastic movable latch with a first side, a second side and a middle region formed as part of the hinge portion, the first side faces the front section and a beak extends therefrom; wherein the beak forms a latch cooperating with the mounting fixture; wherein the fluid pathway aligns with the lumen through the shaft and; wherein pressing on the movable latch lifts the beak out of the mounting fixture.

Aspects of the movable latch may include an active region on one side of the middle region and the inactive region is on the other side of the middle region and wherein the beak extends from the inactive region. In some instances depressing the active region raises the inactive region and beak thereby unlatching the shaft. The moving latch may include physical cues on one of the active and inactive region.

In some exemplars the shaft in cross section has at least a portion that is one of square, hexagon, polygon, circular, and non-circular. In some instances the shaft has a portion that in cross section is circular with one flat axial region. A portion of the guide may be a fixing guide which cooperates with the flat axial section to prevent an inserted shaft from rotating.

In some exemplars the fixing guide cooperates to align the fluid pathway and the shaft lumen.

The above exemplars may have single component handles or the handle may be multipart such as a first handle interface formed opposite the face end; a second handle interface formed on the back half; and, wherein the interfaces cooperate to connect the halves.

The present disclosure provides aspects of a connection system and method including a plastic body with a face end; an interface opening at the face end collinear with a shaft guide configured to accept a shaft; a fluid connection to the fluid pathway in the handle formed at the end terminus of the shaft guide is a guide connection within the handle configured to connect the fluid pathway to the shaft lumen; a beak guide with an open top and an open bottom generally perpendicular to the shaft guide and intersecting the shaft guide; a plastic hinge portion (integrally formed as part of the body); a plastic movable latch with a first side, a second side and a middle region formed as part of the hinge portion; a beak extending from the latch into the beak guide; and, wherein the beak is configured to a latch corresponding mount on a lumentaed shaft. In some instances a shaft with a distal end has a mounting fixture and a proximal end configured to mate with the shaft guide and align the shaft lumen with the fluid pathway; and, wherein the mounting fixture is configured to cooperate with the beak to mount and unmount the shaft. In some instances an active region is formed on one side of the middle region and the inactive region is on the other side of the middle region; and, wherein the beak extends from the inactive region. The system and method may include depressing the active region which raises the inactive region and beak thereby unlatching the shaft. Physical cues on one of the active and inactive region may be added to provide tactile feedback and information regarding operation to a user during operation.

The present disclosure provides aspects of a connection system and method including forming as one piece a plastic movable latch and body connected and a hinge connecting the latch to the body; actuating the movable latch to raise or lower a latching beak within a corresponding open guide in the plastic body; inserting a shaft into a shaft guide in the body which intersects the beak guide; temporarily latching the shaft to the body via a mounting fixture in the shaft with the beak; and, wherein the body has a face end and a tail end. The method may include identifying a portion of the latch to actuate via physical cues. In some instances the method includes placing the active region of the latch which is depressed to raise the beak near the face end; and, wherein a user holding the body grasps near the tail end and is discouraged from inadvertently depressing the active region during grasping.

The fluid pathway may be tapered wherein in addition to it running axially or co-linearly with the guide, it provides a larger diameter cross-sectional opening at the tail end of the handle which tapers into a smaller diameter cross section nearest the terminus of the shaft guide.

The general description and the following detailed description are exemplary and explanatory only and are not restrictive of the disclosure, as defined in the appended claims. Other aspects of the present disclosure will be apparent to those skilled in the art in view of the detailed description of the disclosure as provided herein.

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale.

DRAWINGS

FIG. 1 shows a front section ergonomic quick release device with an attachable back section.

FURTHER DISCLOSURE

Figure 1:
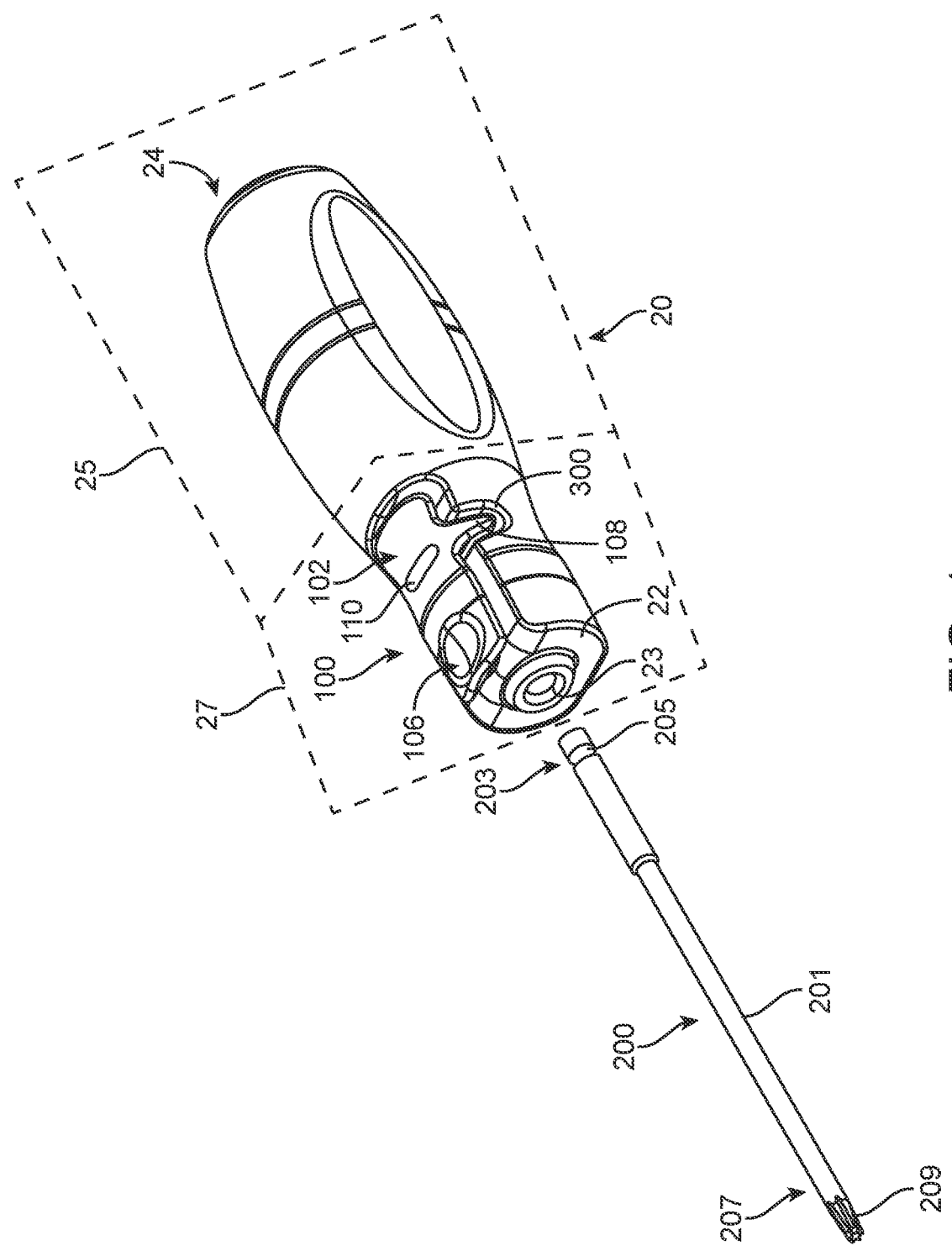
FIG. 1 is a perspective view of aspects of an ergonomic disposable quick release device and system.
Figure 2:
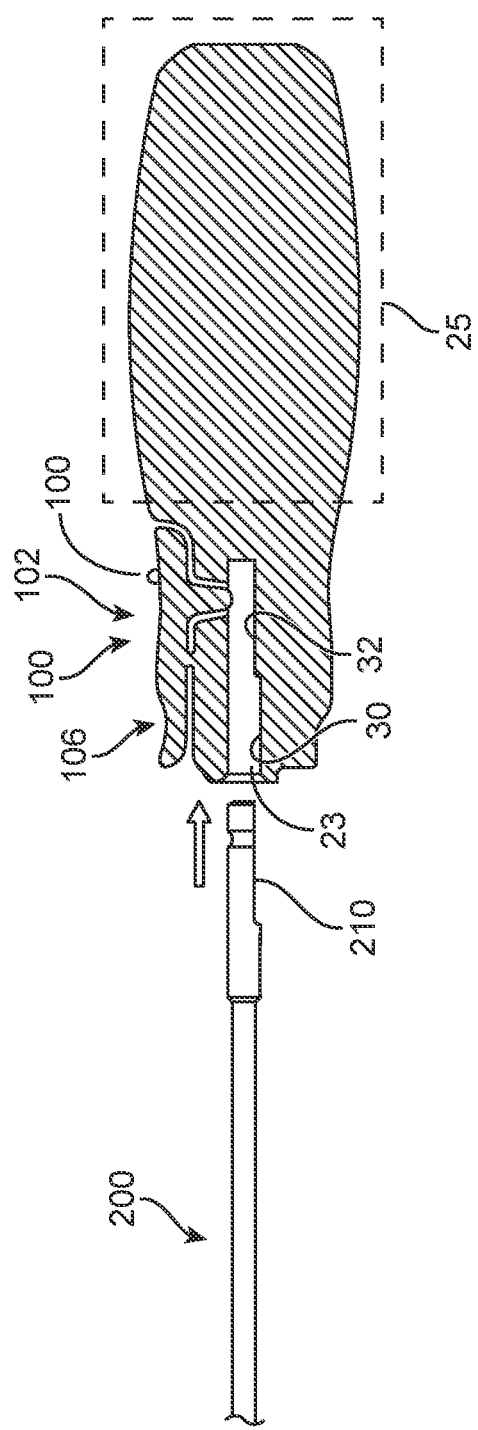
FIG. 2 is a cutaway view of the system of FIG. 1.
Figure 3:
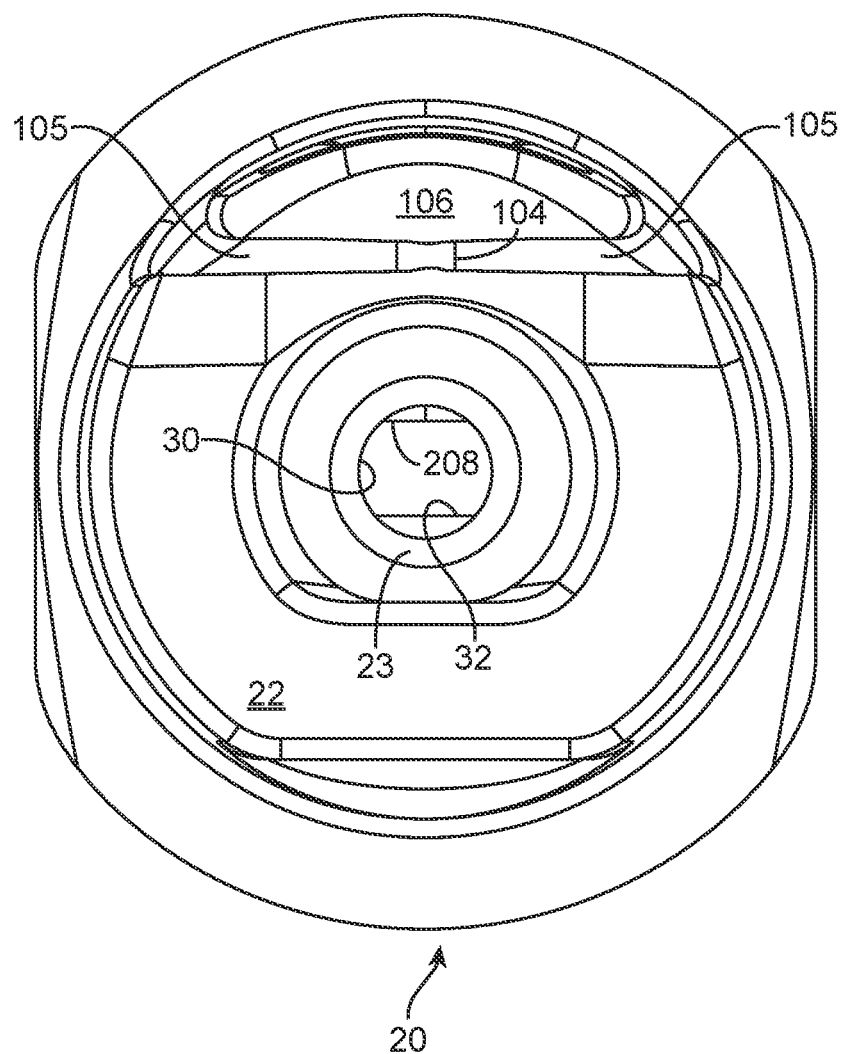
FIG. 3 is a front view of the handle and tool mount shown in FIG. 1.

FIG. 1 shows an exterior perspective view of an exemplar of a disposable quick release system with a tool unmounted. FIGS. 4A, 4B and 7-10 show exterior views of a disposable quick release system with tool mounted.

FIGS. 1-11 illustrate some aspects of exemplary implementations of ergonomic disposable quick release systems and devices.

Disposable tools in a surgical or other medical environments provide single use calibrated devices which require no sterilization or maintenance. While disposable plastic molded devices would not withstand all the harsh rigors of multiple sterilizations, and remain calibrated for hundreds or thousands of uses, they do provide light-weight alternatives. The single piece hinge and lever shown in aspects of the disclosure would be either cost prohibitive or simply not possible if constructed of metal substrates or other materials which can withstand the rigors of reuse, cleaning and sterilization.

FIG. 1 shows an unmounted system 10. The system includes a plastic molded body or handle 20 and a shaft 200. The shaft has a generally elongated body 201 with a distal end 203 having a mounting fixture 205. At the proximal end 207 of the body 201 is a work piece engaging tip 209. The tip may be a tool such as a resector, screw driver, socket or grabbing, other fastening or cutting end. The engaging tip may also be a separate piece (not shown) which mates with the proximal end 207 (not shown).

Figure 11:
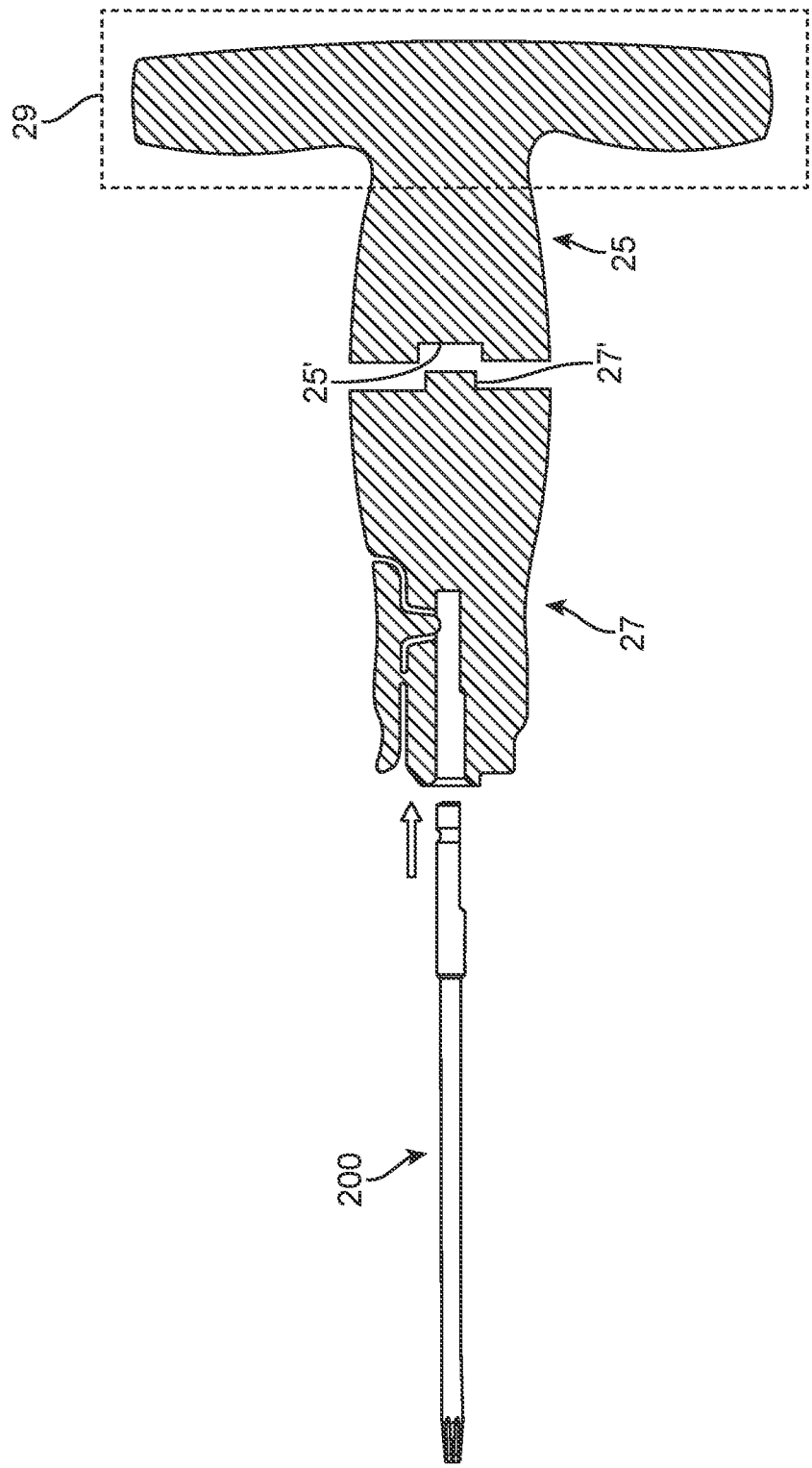

The body 20 has a face end 22 with a shaft mounting interface 23 therein and distal tail end 24. The handle 20 maybe unitary or divided into two or more segments or portions. A back half 25 for gripping and to rotate or otherwise move to impart force to the tip 207. The handle may be configured into a plethora of shapes. A front half 27 wherein the mounting and release of the tool and shaft occurs. Those of ordinary skill in the art will recognize that Included within the disclosure is cylindrical, "T" shaped, polygonal or other designs. It is also within the disclosure as shown in FIG. 11 that the front half 27 may have a first handle interface 27' which is a latch/catch which connects with a second handle interface 25' also part of a latch/catch on the back half. The interfaces may be cooperating threads, latch/catch, bonded, glued or welded, co-molded or otherwise bonded together. These arrangements allow for a single front half with fixation mechanisms to be leveraged and used with a variety of back halves. The front half and back half may be formed of dissimilar materials.

Formed as part of the front half 27 of the handle body is a flat region 28 to provide a physical indication of orientation. Also formed as part of the front half is the integrated movable latch 100. The latch is formed of the same material as the handle at the same time preferably via injection molding. The integrated latch 100 may be further divided into four portions, an inactive region 102 which can be grabbed by a user but will not act to release a shaft 200. A pivot or hinge portion 104 which is integrally formed as part of the handle. The hinge is a thin region of plastic configured to flex when an active region 106 is depressed. The hinge region is a single region of plastic that flexes due to its size and position thereby allowing the latch to raise or lower on either side of it. By depressing the active region 106 a latching beak 108 is lifted from a beak guide 300 whereby the distal end 203 of the shaft may be removed.

The hinge portion, in some exemplars, is sufficient to degrade with usage. In particular because the device is disposable a failure of the hinge will disabuse a user of attempting to reuse the device. In other instances the plastic materials selected to form the hinge are such that they become more brittle and/or have reduced memory when subjected to traditional sterilization methods. In yet other instances the hinge region is frangible and will fail at a predetermined amount of actuations.

Physical cues 110 such as raised ribs may be added to either the inactive region 102 (or conversely the active region 106) to allow a user to feel the area of the lever to depress or identify the area of the lever to avoid.

In operation the latching beak 108 moves generally linearly within the beak guide 300 and functions to reversibly mate with the mounting fixture 205 at the distal end 203 of the shaft. To mount a shaft the distal end 203 is inserted into the mounting interface 23 and then into the shaft guide 30. The distal end 203 reaches the beak 108 and when adequate force is applied the distal end can displace the beak 108 upward allowing the shaft to pass until the mounting fixture 205 catches the beak 108. The active region 106 of the lever is positioned towards the proximal end of the handle. Depressing the active region 106 raises the beak 208 and can be used to insert or withdrawal a shaft. By placing the active region 106 in front of the hinge portion 104 a user is less likely to accidentally release a shaft when grasping the handle. The physical cues 110 although optional also provide a user an indication of where the inactive region of the lever is to avoid unintentional release of shaft.

The shape of the shaft guide 30 is configured to accept shafts with a corresponding shape. Some shafts have a circular cross section with one flat axial segment, other shafts may be polygonal in cross section. FIGS. 2, 3, 5A-6 show a shaft guide 30 configured to accept a shaft with a flat axial section. The guide 30 tapers to a fixing guide 32 which has a flat section corresponding to the flat axial section 210 of the shaft. The fixing guide 32 inhibits rotation of a mounted shaft within the handle. At the closed end or terminus 34 of the guide 30 is an end wall. A guide connection 35 is formed therein configuring the guide to fluidly connect with the fluid pathway 400. Those of ordinary skill in the art will recognize that a polygonal shaft would fit into a guide that was configured to accept a polygonal cross-sectional shaft and such a configuration is within the scope of this disclosure. The flat region 28 is formed as an alignment guide whereby a user will have a physical cue that is parallel with the fixing guide within the front section. Accordingly, a shaft with a flat region may be more easily aligned with the fixing guide.

Figure 5A:
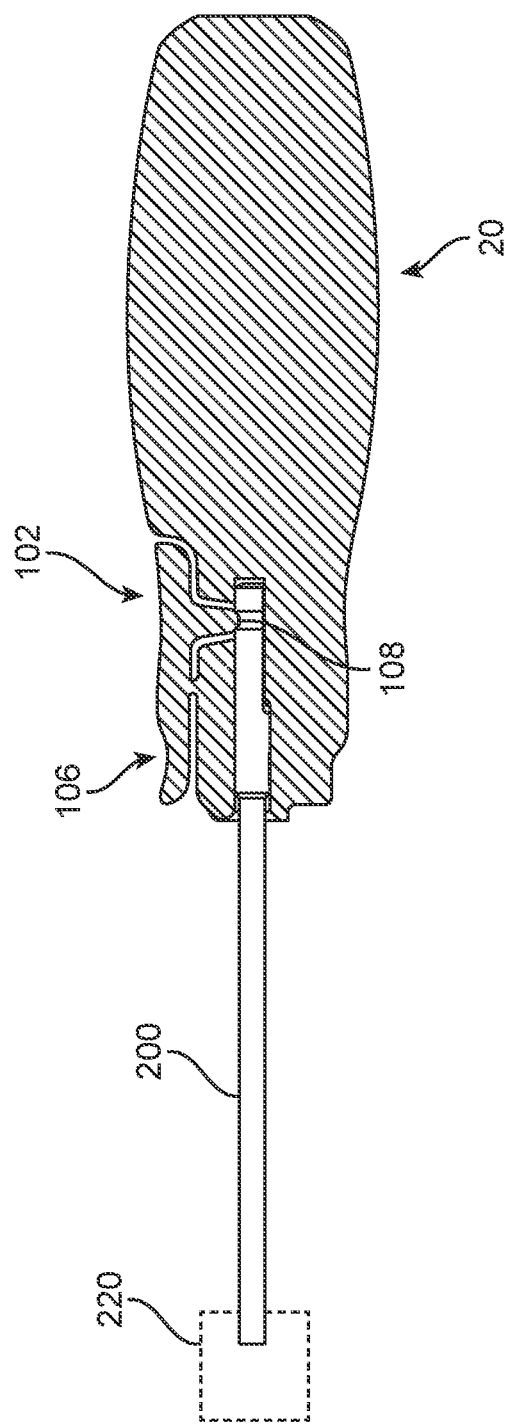
FIGS. 5A-5C are cut-away views of an ergonomic disposable quick release device and system with tool fitted fully into the guide.
Figure 5B:
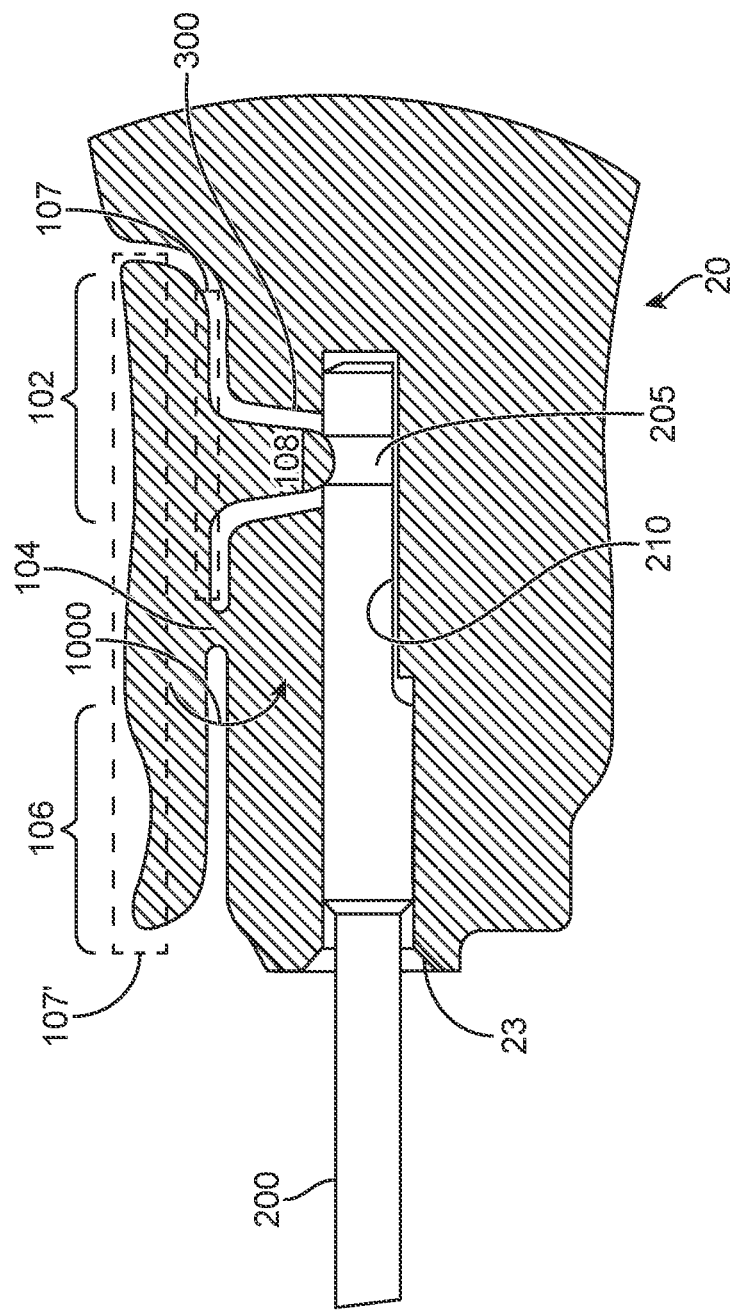
Figure 5C:
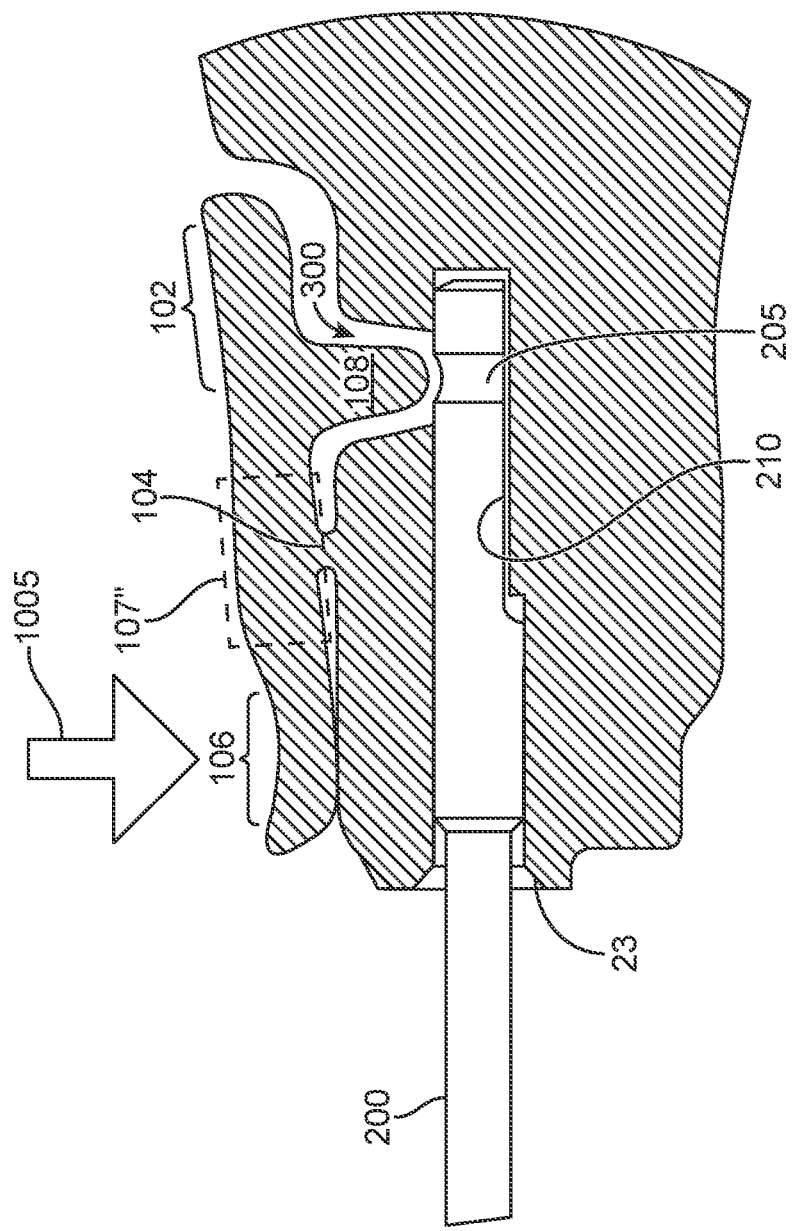

FIG. 5B shows a cut-away close-up of the exemplar shown in FIG. 5A. The movable latch 100 articulates vis a vie the hinge portion 104. Applying pressure to the active region 106 causes the movable latch 100 to rotate about the hinge 104 along the line of arrow 1000 thereby raising the beak 108 from the mounting fixture 205 of the shaft. The beak 108 extends from the first side 107 of the movable latch into a beak guide 300 and connects with the mounting fixture whereby its movement out of the mounting fixture releases the shaft for removal and/or replacement. FIG. 5C shows the unlatching of the shaft when pressure is applied along the line of arrow 1005 to the active region 106. The active and inactive regions are formed on the second side 107' of the latch. The latch connects to the hinge portion 104 at its middle section 107".

Figure 6:
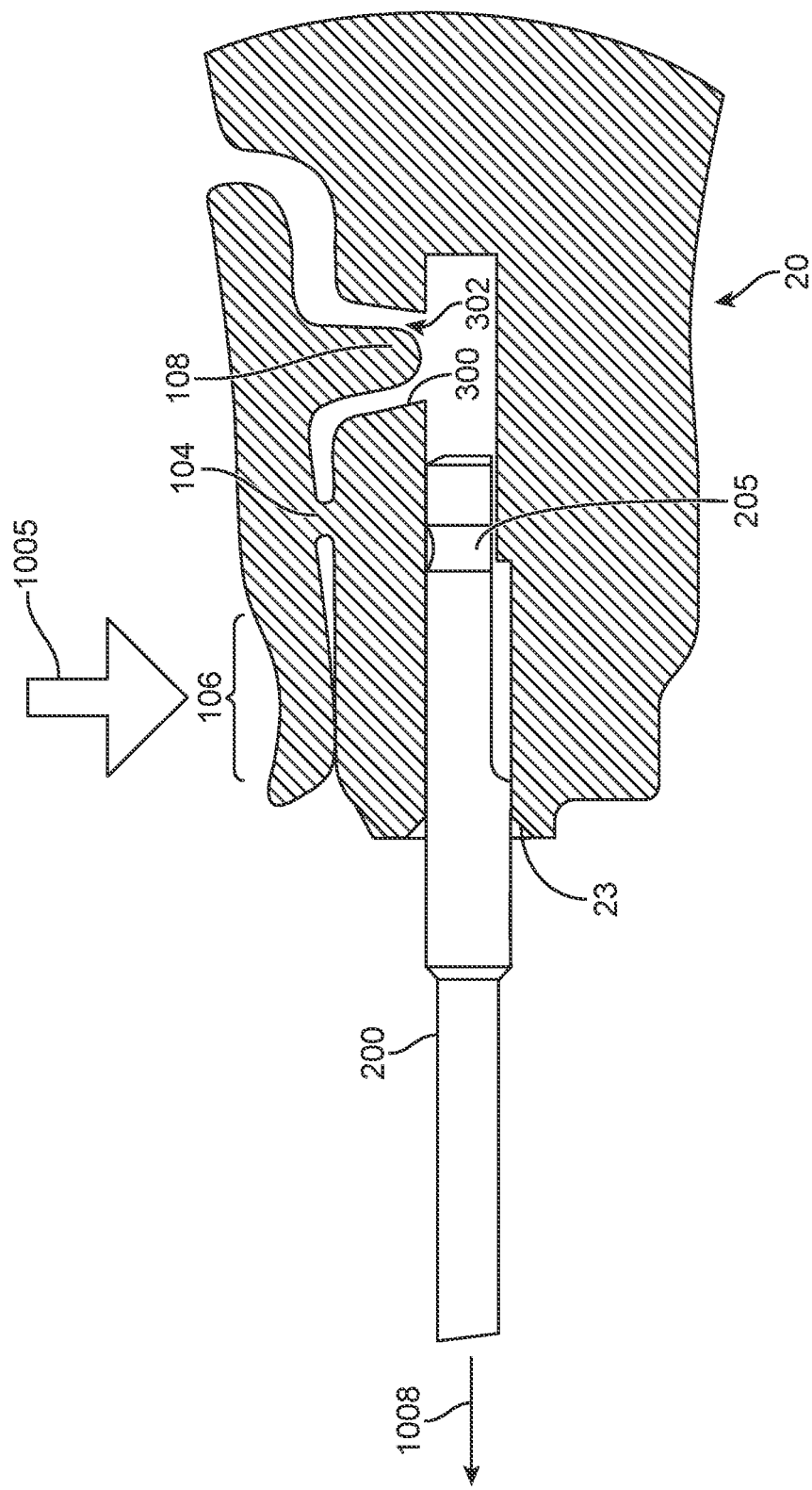
FIG. 6 is a cut-away view of an ergonomic disposable quick release device and system showing tool mount engagement/disengagement.

FIG. 6 shows aspects of a disposable quick release system wherein the shaft 200 is within the shaft guide 30 but not latched via the beak and mounting fixture 205. The beak is raised within the beak guide 300 via force applied to the active region 106 of the movable latch 100. To fix the shaft the user further inserts the shaft into the guide along the line of arrow 1008 until the beak 108 and mounting fixture are connected. To withdraw the shaft the force is applied to the active region 106 to raise the beak 108. The inactive region is illustrated in this exemplary with raised physical cues to provide feedback to the user regarding what portion of the movable latch he/she is in contact with.

Figure 4A:
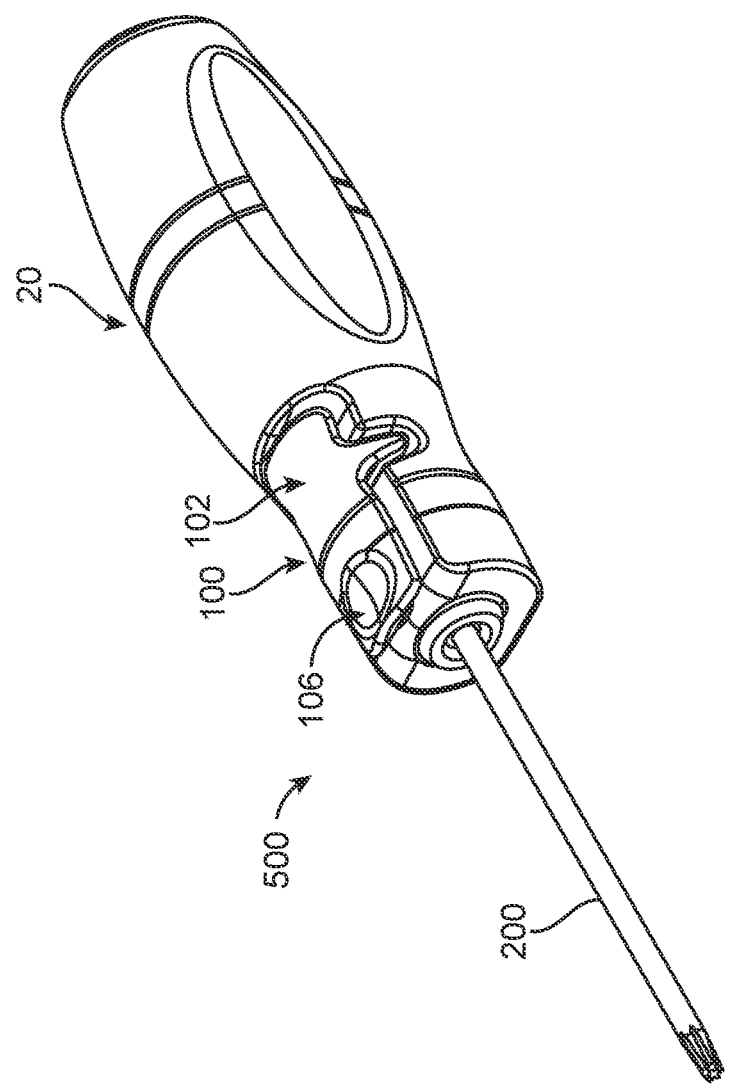
FIGS. 4A and 4B are front and rear perspective views of an ergonomic disposable quick release device and system.
Figure 4B:
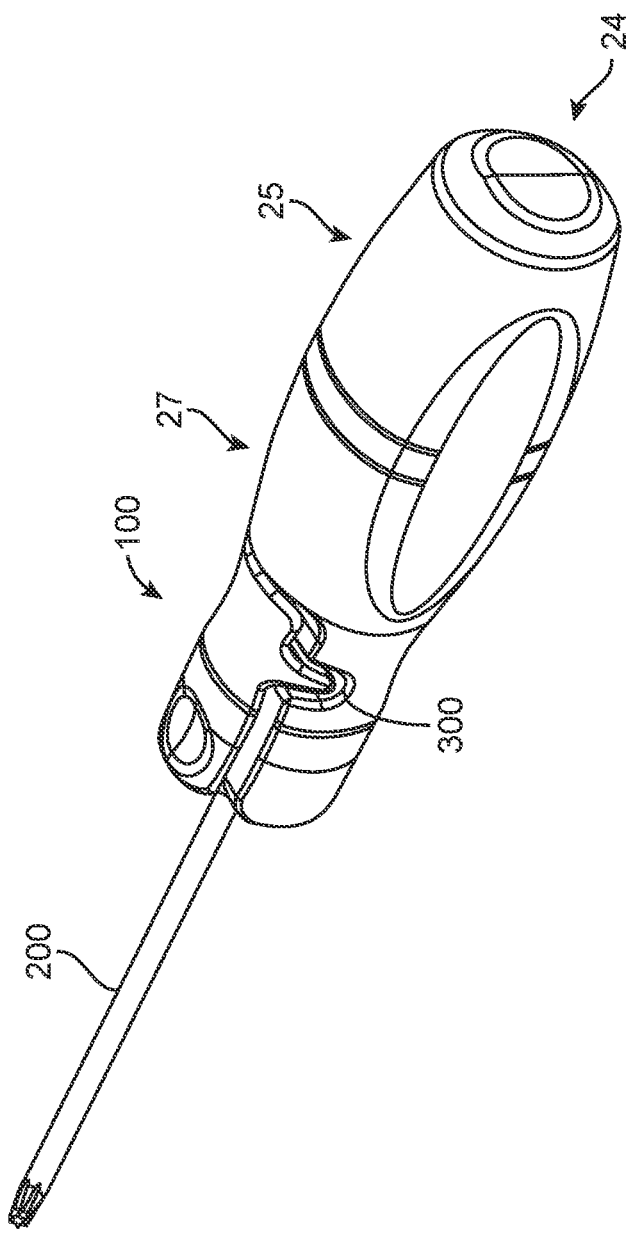
Figure 7:
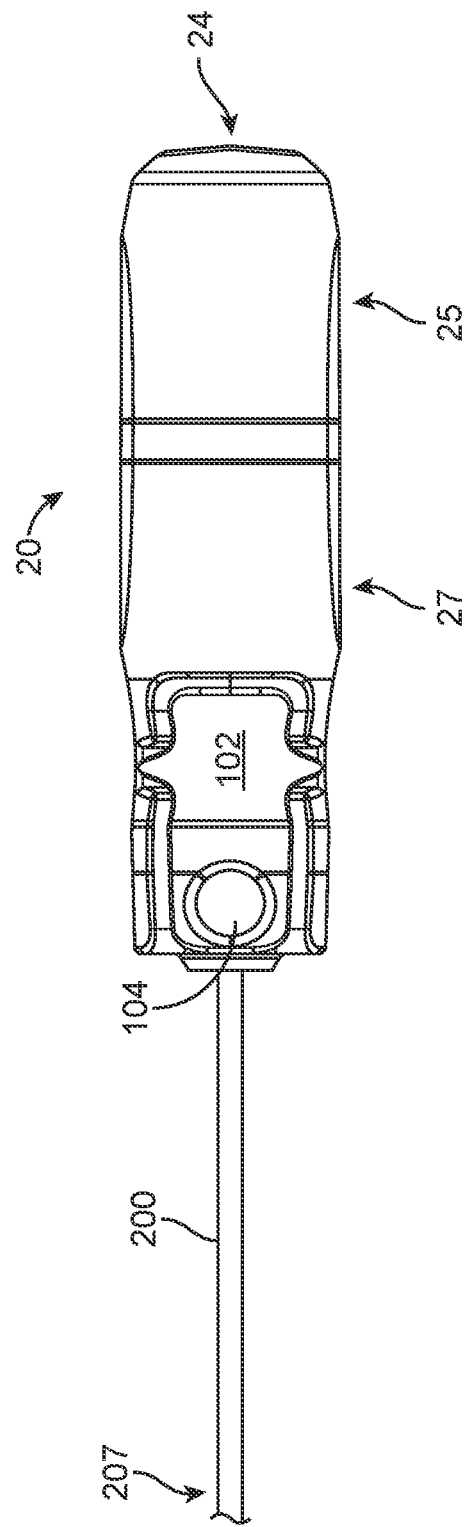
FIG. 7 is atop view of an ergonomic disposable quick release device and system with tool mount.
Figure 8:
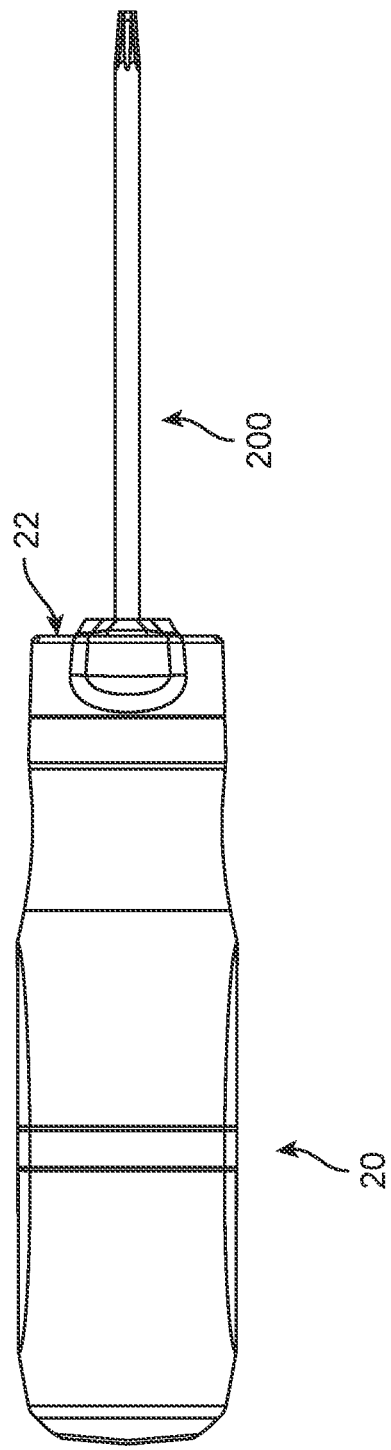
FIG. 8 is a bottom view of an ergonomic disposable quick release device and system with tool mounted.
Figure 9:
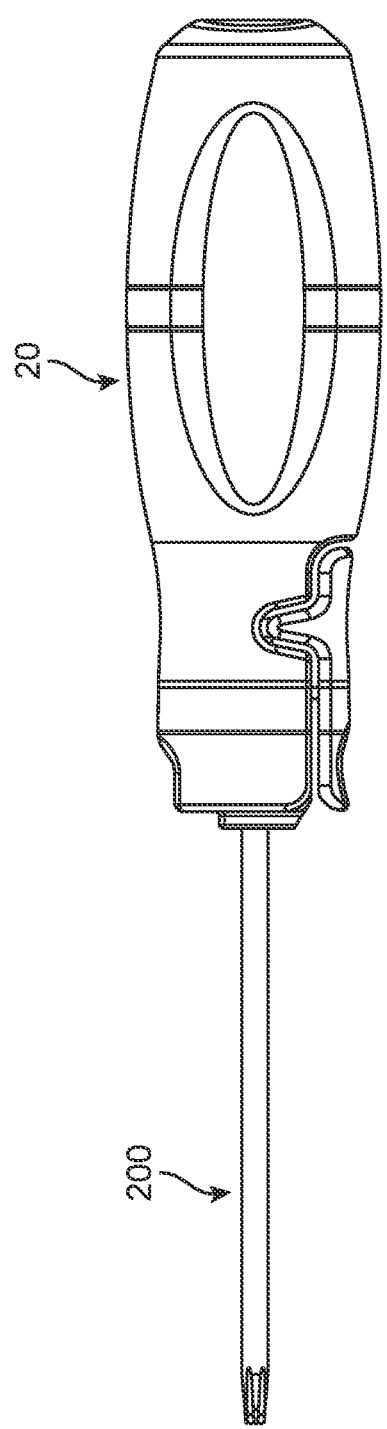
FIG. 9 is a side view of an ergonomic disposable quick release device and system with tool mounted.

FIGS. 4A and 4B show two perspective views of the disposable quick release device 500. FIGS. 7 through 9 show top, front, back, bottom and side views of aspects of disposable quick release devices and systems. The tool 220 affixed at the proximal end 207 of the shaft 200 is shown as a block to indicate it may be a blade, socket, or the like. Those of ordinary skill in the art will recognize that a variety of tools may be connected to or formed integral to the shaft. The block also denotes a mounting interface to connect said tool(s).

Figure 10A:
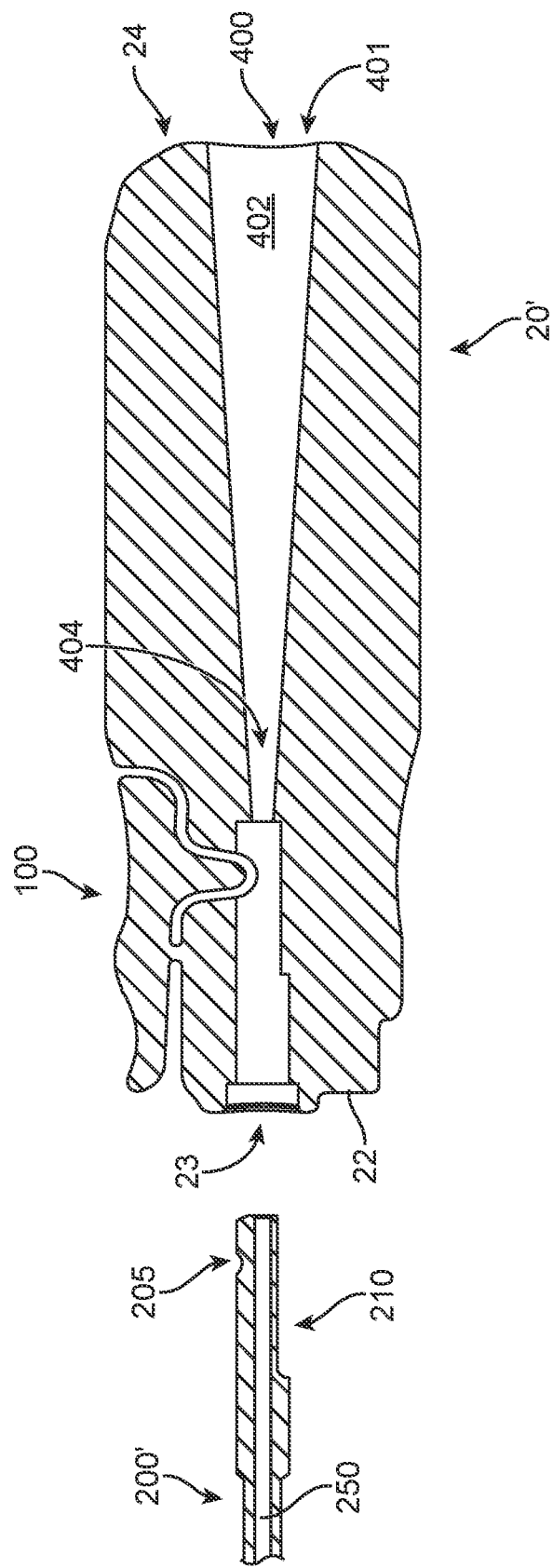
FIG. 10A-10C are cut-away views along the axial line of cannulated disposable ergonomic devices.
Figure 10B:
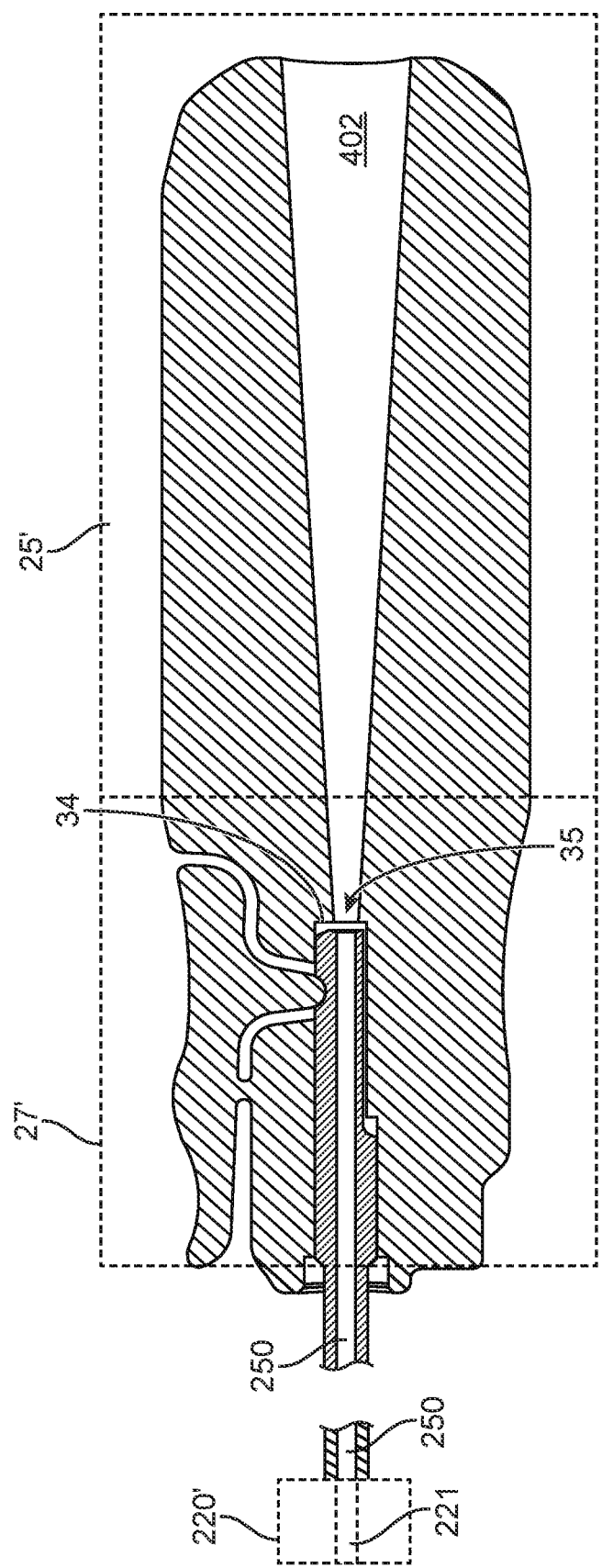
Figure 10C:
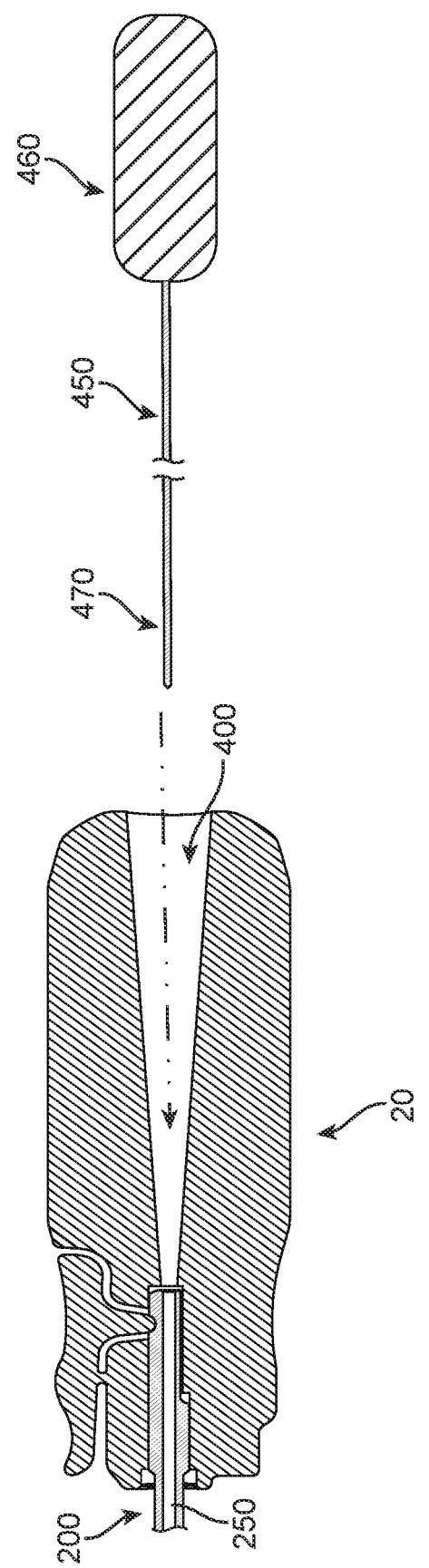

FIGS. 10A-10C illustrate aspects of cannulated disposable quick release devices. The handle 20' may be similar to the handle 20 and has similar functionality with respect to the latching of the shaft 200.

A cannulated device and system supports a method of utilizing a removable, disposable or otherwise swappable inner tool. The handle 20' (both the front section 27' and the back section 25') have an axial cavity forming a fluid pathway 400 running or spanning axially from the tail end 24 to the guide's closed end 34. The fluid pathway 400 may be referred to as a guide, lumen or cannula. The fluid pathway is configured for the insertion and removal of tools, additive or for evacuation tools and device.

The inner tool 450 is configured to be inserted through the fluid pathway or cannula 400 into another pathway/lumen 250 formed through the shaft 200' and the tool 220'. The system includes a mountable, swappable, and/or disposable shaft 200' with a lumen 250 therethrough which allows for the insertion of a tool 450. In some instance a tool 220' is affixed to the shaft 200' and the lumen fluidly connects to the tool lumen 221.

Those of ordinary skill in the art will recognize that the tool will include, but not be limited to resector, files, prods, picks, syringes, fastening devices which may be used for cutting, resecting, sampling tissue or fluid, adding fluids, adding organic or inorganic materials such as cements, adhesives, antibiotics and the like.

The inner tool 450 has a proximal end 460 which may be used as a handle, syringe pump or grip and a distal end 470 which engages with the site the tool 220 interacts with. The distal end is inserted into the cannula 400. The insertion point is at the tail end 24 of the handle 20'. The fluid pathway 400 has a larger diameter opening 402 nearest the tail end which may taper into a smaller diameter end 404 which is fluidly connected to the guide's closed end 34.

The tapered cannula may be configured to align the distal end 470 with the lumen 250 of the shaft 200'. The additional benefit of said alignment is to protect the distal end 470 from shock or stress during insertion.

FIG. 11 shows a modular ergonomic quick release device and system. This exemplar illustrates that the front half 27 with a first handle interface 27' that cooperates with the back half 25 at the back handle interface 25' by connecting thereto. The interface shown is a latch/catch. However, those of ordinary skill in the art will recognize that a plethora of connection interfaces may be used including but not limited to adhesive, bonding, sonic welds, threads, friction locks and the like, all of which are within the scope of this disclosure. In some instances a "T" shaped portion 29 may be formed as part of the back half.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest editions of which are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A connection method to connect a shaft to a body, the method comprising:
    forming, as one piece, a plastic movable latch and a body connected by a hinge;
    actuating the movable latch to raise or lower a latching beak within a corresponding open beak guide in the plastic body;
    inserting a shaft having a lumen running axially into a shaft guide in the body which intersects said beak guide;
    temporarily latching the shaft to the body via a mounting fixture in the shaft with said latching beak;
    wherein the body has a face end and a tail end; and,
    wherein a fluid pathway having a larger diameter towards said tail end and a smaller diameter towards said face end is formed axially through said body and configured to fluidly connect through the guide connection to the shaft's lumen.

2. The method of claim 1, the method further comprising identifying a portion of the latch to actuate via physical cues.

3. The method of claim 1, the method further comprising placing the active region of the latch which is depressed to raise the beak near the face end; and,
    wherein a user holding the body grasps near the tail end and is discouraged from inadvertently depressing the active region during grasping.

4. An ergonomic quick release system comprising:
    a plastic molded handle having a front half comprising a front section and a back half comprising a back section and a tail end;
    a fluid pathway having a larger diameter towards said back section and a smaller diameter towards said front section formed axially from said tail end to an open guide connection;
    a face end with an interface;
    a shaft guide collinear with the interface configured to accept a shaft;
    a beak guide with an open top and an open bottom;
    a plastic flexible hinge portion integrally formed as part of the front half of said handle;
    a plastic movable latch with a first side, a second side and a middle region formed as part of said hinge portion;
    wherein the first side faces the front section and a beak extends therefrom;
    wherein said beak forms a latch cooperating with a mounting fixture; and,
    wherein pressing on the movable latch lifts said beak out of said mounting fixture.

5. The system of claim 4 further comprising:
    an active region on one side of said middle region and an inactive region on the other side of said middle region; and,
    wherein said beak extends from the inactive region.

6. The system of claim 5 further comprising:
    a shaft with a proximal end having a mounting fixture and a distal end configured to mate with said shaft guide and a lumen formed axial through said shaft;
    wherein said beak forms a latch cooperating with said mounting fixture; and,
    wherein pressing on said movable latch lifts said beak out of said mounting fixture.

7. The system of claim 6 wherein depressing said active region raises said inactive region and beak thereby unlatching said shaft.

8. The system of claim 6 wherein:
    said shaft in cross section has at least a portion that is one of square, hexagon, polygon, circular and non-circular; and,
    wherein said cross section is configured to align said lumen with the fluid pathway in the handle.

9. The system of claim 8 wherein said shaft has a portion that in cross section is circular with one flat axial region.

10. The system of claim 9 wherein a portion of said shaft guide is a fixing guide which cooperates with the flat axial region to prevent an inserted shaft from rotating.

11. The system of claim 6 wherein said fluid pathway is tapered having a larger diameter opening nearest the tail end which is reduced into a smaller diameter end which is fluidly connected to the shaft guide's closed end.

12. The system of claim 5 further comprising physical cues on one of the active and inactive region.

13. The system of claim 4 wherein said molded handle is a single component and the back half is "T" shaped.

14. The system of claim 4 wherein said molded handle is at least two components and the back section is one of elongated and "T".

15. The system of claim 14 further comprising:
a first handle interface formed opposite the face end;
a second handle interface formed on the back half; and,
wherein said interfaces cooperate to connect the halves.

16. The system of claim 4 further comprising an insertable inner tool with a proximal end and a distal end; and,
wherein the distal end is inserted into the fluid pathway through the handle and shaft and is configured to extend through an attached tool associated with the shaft.

17. A quick release connection comprising:
a body having a front section, a back section, and a fluid pathway having a larger diameter towards said back section and a smaller diameter towards said front section formed axially therethrough;
an interface opening at the face end of said front section of said body which is collinear with a shaft guide configured to accept a shaft; a beak guide with an open top and an open bottom generally perpendicular to said shaft guide and intersecting said shaft guide;
a plastic hinge portion integrally formed as part of said body;
a plastic movable latch with a first side, a second side and a middle region formed as part of said hinge portion;
a beak extending from said latch into said beak guide; and,
wherein said beak is configured to a latch a corresponding mounting fixture on a shaft.

18. The quick release connection of claim 17 further comprising:
a shaft with a proximal end having said mounting fixture and a distal end configured to mate with said shaft guide;
a tool with a tool lumen there through affixed to the proximal end of said shaft; and,
wherein said mounting fixture is configured to cooperate with said beak to mount and unmount said shaft.

19. The quick release connection of claim 17 further comprising:
an active region on one side of said middle region and said inactive region is on the other side of said middle region; and,
wherein said beak extends from said inactive region.

20. The quick release connection of claim 17 wherein depressing said active region raises said inactive region and beak thereby unlatching said shaft.

21. The quick release connection of claim 19 further comprising physical cues on one of said active and inactive region.

* * * * *